United States Patent [19]

Goldstein et al.

[11] Patent Number: 5,234,001
[45] Date of Patent: Aug. 10, 1993

[54] CONTAINER FOR IMMUNOASSAY WITH FRANGIBLE NIPPLE

[75] Inventors: Andrew S. Goldstein; David F. Zogg, both of Beaverton, Oreg.

[73] Assignee: Epitope, Inc., Beaverton, Oreg.

[21] Appl. No.: 863,756

[22] Filed: Apr. 6, 1992

Related U.S. Application Data

[63] Continuation-in-part of Ser. No. 641,739, Jan. 15, 1991, Pat. No. 5,103,836, which is a continuation-in-part of Ser. No. 486,415, Feb. 28, 1990, abandoned, which is a continuation-in-part of Ser. No. 410,401, Sep. 21, 1989, Pat. No. 5,022,409.

[51] Int. Cl.⁵ .................................. A61B 5/00
[52] U.S. Cl. ........................... 128/760; 604/403
[58] Field of Search ............ 128/760, 766; 604/317, 604/403, 405, 406, 905; 206/569

[56] References Cited

U.S. PATENT DOCUMENTS

| | | | |
|---|---|---|---|
| 1,718,590 | 6/1929 | Smith | 604/403 |
| 1,993,629 | 5/1935 | Smith | 604/403 |
| 3,750,645 | 8/1973 | Bennett et al. | 128/760 |
| 4,580,577 | 4/1986 | O'Brien et al. | 128/760 |
| 4,774,962 | 10/1988 | Hebel et al. | 128/760 |

FOREIGN PATENT DOCUMENTS 3018262  11/1981  Fed. Rep. of Germany ...... 128/766

Primary Examiner—Max Hindenburg
Attorney, Agent, or Firm—Wegner, Cantor, Mueller & Player

[57] ABSTRACT

A container for storing collected substances for subsequent testing having an open upper end adapted to be sealed with a removable stopper and a lower end having an opening communicating the interior of the container with the outside. The opening is selectively sealed by a frangible nipple during storage of the substances and unsealed for removal of the collected substances for subsequent testing. The distal end of the frangible nipple is enlarged, preferably in the form of a ball.

7 Claims, 2 Drawing Sheets

CONTAINER FOR IMMUNOASSAY WITH FRANGIBLE NIPPLE

CROSS-REFERENCE TO RELATED APPLICATIONS

This application is a continuation-in-part of co-pending application Ser. No. 641,739, filed Jan. 15, 1991 Pat. No. 5,103,836 which, in turn, is a continuation-in-part of application Ser. No. 486,415, filed Feb. 28, 1990, now abandoned which is a continuation-in-part of application Ser. No. 410,401, filed Sep. 21, 1989, now Pat. No. 5,022,409.

BACKGROUND OF THE INVENTION

This invention relates to containers this invention relates to containers for collecting samples to be used for immunoassay and other analyte detectron.

A system for analyzing immunoglobulins, detecting hormones, therapeutic drug levels, drugs of abuse and other substances extracted from the oral cavity utilizing a pad and embodiments of a container for collecting samples to be used for an immunoassay are disclosed in co-pending application Ser. No. 641,739, which is incorporated herein in its entirety by reference. One of the embodiments is a container in the form of a tube having a frangible nipple at the lower end. The tube has an open upper end forming an outwardly projecting annular rim or bead and a lower end forming a floor. The wall is preferably slightly tapered from the upper end to the floor. A nipple extends downwardly from the floor. At the center of the inside of the floor is a depression, preferably "V" shaped. The depression causes the base end of nipple to be weakened, thereby allowing the same to break off when sufficient pressure is applied. The floor preferably has a slight slope from the outside to the center. The container could be made of any suitable material such as polypropylene, polyethylene, polyethylene terephthalate (PET, PETG), polystyrene polycarbonate, glass, etc.

It has been found that breaking of the frangible nipple of the previous construction causes discomfort in the user due to the small size and the shape. There is also the possibility, however small, of injury to the user when the nipple is broken off.

The previous container was designed for use with a stopper of complex configuration. The stopper is hollow and comprises an upper shank portion which is closed at its upper end, the top extending radially outwardly to define an annular flange which is provided for gripping the stopper to remove it from the container. The diameter of the upper shank portion is approximately the same as that of the bead of the container. The upper shank portion terminates at its lower end in an annular shoulder. The lower shank portion extends downwardly from the shoulder.

A plurality of annular beads are formed on the lower shank portion. The lowest bead is pointed with the upper and lower faces being at different angles. The upper and lower faces are at different angles from the horizontal. The lower face tapers downwardly and inwardly from the apex of the bead to the inner wall of the stopper. The intermediate bead is also pointed with its upper and lower faces at different angles, preferably the same angles as the upper and lower faces of the bead. The upper bead, however, is shaped differently. The upper bead comprises a linear upper face, an essentially vertical linear middle face, and a linear lower face.

Not only is the configuration of the stopper complex, it has been found to be difficult to remove from, and replace in, the container.

SUMMARY OF THE INVENTION

It is, therefore, the object of the present invention to provide a container of the type described which is free of the aforementioned and other such disadvantages.

Consistent with the foregoing object, the container for storing collected substances for subsequent testing of the present invention comprises an open upper end adapted to be sealed with a removable stopper and a lower end having an opening communicating the interior of the container with the outside, the opening being selectively sealed by a frangible nipple during storage of the substances and unsealed for removal of the collected substances for subsequent testing. For both comfort and safety of the user, the distal end of the frangible nipple is enlarged, preferably in the form of a ball. The open upper end is preferably sealed with a screw-on "plug seal" cap. In addition, the floor of the container, which slopes towards the opening in the center thereof, has a plurality of upstanding webs to prevent the pad described in the aforementioned application Ser. No. 641,739 from resting on the bottom of the container and blocking the opening at the bottom.

The container is dimensioned to permit its insertion into a standard 15 ml. conical centrifuge tube. This allows centrifugation after the nipple is broken off, thereby transferring the vial contents into the centrifuge tube.

The container is intended to hold a volume of preservative liquid (from about 0.5 ml. to about 2.0 ml.). When the pad is placed in the container, the preservative is absorbed into the pad. Since the container with the preservative will be stored for up to a year without significant loss of liquid volume, the water transmission rate must be low. The container is fabricated of any suitable plastic such as polyethylene, polycarbonate, polystyrene, PET (polyethylene terephthalate), polypropylene, EPC (ethylene propylene copolymer), and the like. Polycarbonate is the least desirable due to excessive "breathing," that is, allowing moisture to escape. The preferred material is polypropylene.

BRIEF DESCRIPTION OF THE DRAWINGS

The invention itself, as well as additional advantages and features thereof, will be more readily and comprehensively understood from the following detailed description of the preferred embodiments, such description making reference to the appended sheets of drawings, wherein.

DESCRIPTION OF THE PREFERRED EMBODIMENTS

Figure 2:
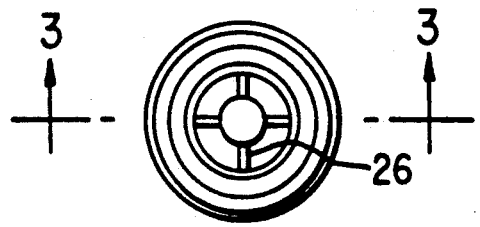
FIG. 2 is a top plan view of the container of FIG. 1.
Figure 1:
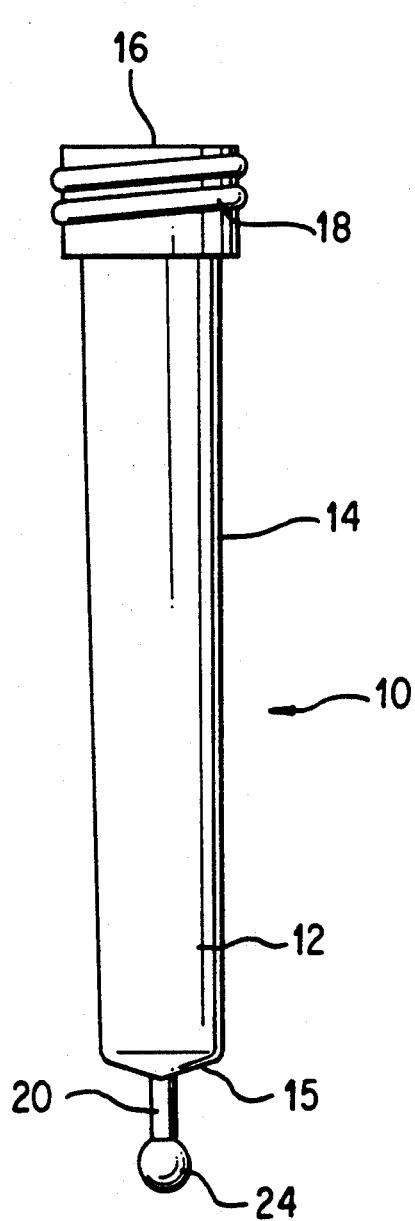
FIG. 1 is an elevational view of the container of the present invention with the cap removed.
Figure 3:
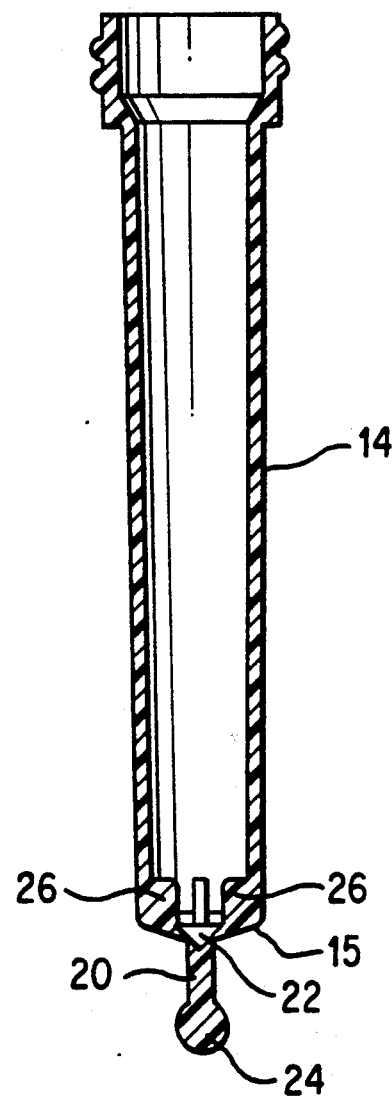
FIG. 3 is a longitudinal cross-sectional view of the container of the present invention taken along the line 3—3 of FIG. 2.

Referring first to FIGS. 1 and 2, the container of the instant invention, generally designated by the numeral 10, comprises an elongated body portion 12. Body portion 12 is generally cylindrical although, it is preferably slightly tapered from the upper end to the floor 15. The upper end 16 is open and is provided with a screw thread 18 to accommodate the cap.

A nipple 20, 24 extends downwardly from the floor 15. The floor 15 preferably has a slight slope at an angle $\alpha$ from the outside to the center. Angle $\alpha$ is preferably about 20°. At the center of the inside of the floor 15 is a depression 22, preferably "V" shaped and preferably forming an angle of about 88.50°. The depression 22 causes the base end of nipple 20 to be weakened, thereby allowing the same to break off when sufficient pressure is applied. The nipple comprises an elongated stem portion 20 terminating in an enlarged portion, or bulb 24 which is formed at the distal end to make it easier and safer to break off the frangible nipple.

In order to prevent the pad which will be inserted in the container 10 from resting on the floor 15 at the hold created by breaking off nipple 20, a plurality of upstanding webs 26 are provided on floor 15. Preferably, there are four webs 26.

Figure 4:
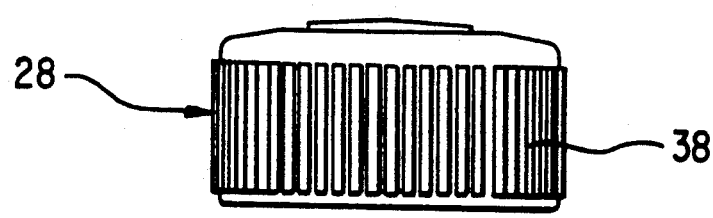
FIG. 4 is an elevational view of a cap for use with the container shown in FIG. 1.
Figure 5:
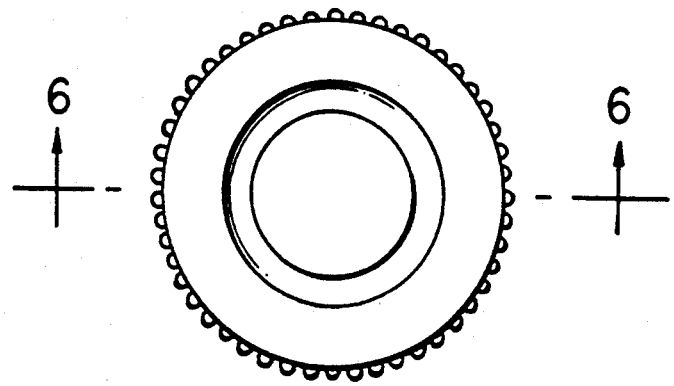
FIG. 5 is a top plan view of the cap of FIG. 4.
Figure 6:
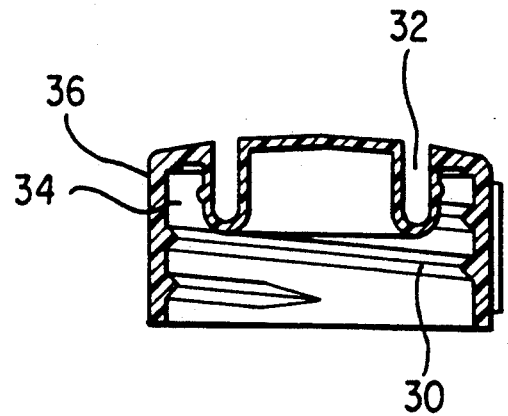
FIG. 6 is a cross-sectional view of the cap taken along the line 6—6 of FIG. 5.

Turning now to FIGS. 4, 5, and 6, there is shown a cap, generally designated by the numeral 28 for sealing the open upper end 16 of container 10. Cap 28 is of the type commonly known as a "plug seal" cap. Cap 28 has internal screw threads 30 to cooperate with threads 18 on the container. Annular depression 32 creates an annular space 34 bounded by annular depression 32 and the inside of outer wall 36. The wall of the container thus fits into annular space 34 and creates a perfect seal.

The outside surface of cap 28 is knurled as shown at 38 to facilitate removal and replacement of the cap.

The container 10 is used in the same manner as the containers taught by the aforementioned co-pending application Ser. No. 641,739. As with the embodiments of the parent application, the container 10 could be sold in kit form along with the impregnated pad and holder.

What is claimed is:

1. A container for storing collected substances for subsequent testing comprising an open upper end adapted to be sealed with a removable stopper and a lower end having an opening communicating the interior of the container with the outside, said opening being selectively sealed by a frangible nipple during storage of the substances and unsealed for removal of the collected substances for subsequent testing, said frangible nipple comprising an elongated stem portion terminating in an enlarged end portion.

2. A container as defined in claim 1, wherein said enlarged end portion of said frangible nipple is in the form of a generally spherical ball.

3. A container as defined in claim 1, wherein the lower end of said container comprises a floor and said floor slopes downwardly toward the middle thereof, said nipple extending downwardly from said floor.

4. A container as defined in claim 3, further comprising a plurality of spaced apart webs upstanding from said floor.

5. A container as defined in claim 1, further comprising a central depression in said floor.

6. A container as defined in claim 1, wherein said depression is "V" shaped.

7. A kit for collecting and storing substances from an oral cavity for subsequent testing comprising a pad and the container of claim 1.

* * * * *